(12) United States Patent
Slazas et al.

(10) Patent No.: US 10,786,378 B2
(45) Date of Patent: Sep. 29, 2020

(54) CAPTURE TUBE MECHANISM FOR DELIVERING AND RELEASING A STENT

(71) Applicant: DEPUY SYNTHES PRODUCTS, INC., Raynham, MA (US)

(72) Inventors: Robert Slazas, Pinecrest, FL (US); Juan Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 171 days.

(21) Appl. No.: 16/148,392

(22) Filed: Oct. 1, 2018

(65) Prior Publication Data

US 2019/0029856 A1    Jan. 31, 2019

Related U.S. Application Data

(62) Division of application No. 13/801,728, filed on Mar. 13, 2013, now Pat. No. 10,172,734.

(51) Int. Cl.
| | | |
|---|---|---|
| *A61F 2/97* | (2013.01) | |
| *A61F 2/966* | (2013.01) | |
| *A61F 2/95* | (2013.01) | |
| *A61F 2/82* | (2013.01) | |

(52) U.S. Cl.
CPC ............. *A61F 2/97* (2013.01); *A61F 2/966* (2013.01); *A61F 2/82* (2013.01); *A61F 2002/9511* (2013.01); *A61F 2002/9534* (2013.01); *A61F 2002/9665* (2013.01)

(58) Field of Classification Search
CPC ...... A61F 2002/9534; A61F 2002/9511; A61F 2/966; A61F 2/97; A61F 2/82
See application file for complete search history.

(56) References Cited

U.S. PATENT DOCUMENTS

| | | | | |
|---|---|---|---|---|
| 4,732,152 | A | * | 3/1988 | Wallsten ............... A61F 2/95 604/271 |
| 4,913,141 | A | | 4/1990 | Hillstead |
| 5,019,085 | A | | 5/1991 | Hillstead |
| 5,192,297 | A | | 3/1993 | Hull |
| 5,201,757 | A | * | 4/1993 | Heyn ................ A61F 2/97 606/198 |
| 5,304,194 | A | * | 4/1994 | Chee .............. A61B 17/12022 604/104 |
| 5,405,378 | A | | 4/1995 | Strecker |
| 5,549,122 | A | | 8/1996 | Detweilwer |

(Continued)

FOREIGN PATENT DOCUMENTS

| | | |
|---|---|---|
| CN | 101879103 A | 11/2010 |
| CN | 102271626 A | 12/2011 |

(Continued)

*Primary Examiner* — Phong Son H Dang

(57) ABSTRACT

A capture tube mechanism for delivering and releasing a self-expanding stent includes a core wire on which a proximal portion of the stent is removably retained by a distal portion of a tubular capture sleeve. In one embodiment, one or more elongated members extending through corresponding apertures through the capture sleeve and out the distal end of the capture sleeve can be pulled to split the tubular capture sleeve to release the stent. In another embodiment, the capture sleeve can be pulled proximally over one or more stop members provided on the core wire to release the stent.

12 Claims, 4 Drawing Sheets

(56) References Cited

U.S. PATENT DOCUMENTS

| | | | |
|---|---|---|---|
| 5,639,277 A * | 6/1997 | Mariant | A61B 17/12022 606/191 |
| 5,649,949 A * | 7/1997 | Wallace | A61B 17/12022 600/200 |
| 5,683,451 A * | 11/1997 | Lenker | A61F 2/91 623/1.11 |
| 5,733,329 A * | 3/1998 | Wallace | A61B 17/12022 606/158 |
| 5,749,891 A * | 5/1998 | Ken | A61B 17/12022 606/200 |
| 5,824,055 A | 10/1998 | Spiridigliozzi | |
| 5,911,731 A * | 6/1999 | Pham | A61B 17/12022 140/92.1 |
| 5,935,148 A * | 8/1999 | Villar | A61B 17/12022 606/213 |
| 6,033,423 A * | 3/2000 | Ken | A61B 17/12022 606/200 |
| 6,036,720 A * | 3/2000 | Abrams | A61B 17/12022 606/200 |
| 6,110,180 A | 8/2000 | Foreman | |
| 6,143,016 A | 11/2000 | Bleam | |
| 6,254,612 B1 | 7/2001 | Hieshima | |
| 6,468,298 B1 | 10/2002 | Pelton | |
| 6,612,012 B2 | 9/2003 | Mitelberg | |
| 6,635,069 B1 * | 10/2003 | Teoh | A61B 17/12022 606/191 |
| 6,638,291 B1 * | 10/2003 | Ferrera | A61B 17/12022 606/191 |
| 6,669,719 B2 * | 12/2003 | Wallace | A61F 2/962 623/1.12 |
| 6,673,106 B2 | 1/2004 | Mitelberg | |
| 6,802,851 B2 * | 10/2004 | Jones | A61B 17/12022 606/200 |
| 6,818,013 B2 | 11/2004 | Mitelberg | |
| 6,833,003 B2 | 12/2004 | Jones | |
| 6,955,685 B2 | 10/2005 | Escamilla | |
| 6,960,227 B2 | 11/2005 | Jones | |
| 6,960,228 B2 | 11/2005 | Mitelberg | |
| 7,001,422 B2 | 2/2006 | Escamilla | |
| 7,037,331 B2 | 5/2006 | Mitelberg | |
| 7,320,703 B2 | 1/2008 | DiMatteo | |
| 7,691,109 B2 | 4/2010 | Armstrong | |
| 7,879,064 B2 * | 2/2011 | Monstadt | A61B 17/12022 606/200 |
| 8,088,154 B2 * | 1/2012 | Hoffman | A61F 2/95 623/1.11 |
| 8,721,714 B2 * | 5/2014 | Kelley | A61F 2/2436 623/2.11 |
| 8,852,257 B2 * | 10/2014 | Liu | A61F 2/97 623/1.11 |
| 8,998,973 B2 * | 4/2015 | Molaei | A61F 2/07 623/1.13 |
| 9,675,482 B2 * | 6/2017 | Becking | A61F 2/97 |
| 2001/0056295 A1 | 12/2001 | Solem | |
| 2002/0019647 A1 * | 2/2002 | Wallace | A61B 17/12145 606/200 |
| 2002/0045930 A1 | 4/2002 | Burg | |
| 2003/0105508 A1 * | 6/2003 | Johnson | A61F 2/958 623/1.11 |
| 2004/0098027 A1 * | 5/2004 | Teoh | A61B 17/12172 606/200 |
| 2004/0133261 A1 | 7/2004 | Bigus | |
| 2004/0143315 A1 * | 7/2004 | Bruun | A61F 2/966 623/1.11 |
| 2005/0043757 A1 | 2/2005 | Arad | |
| 2005/0049669 A1 | 3/2005 | Jones | |
| 2005/0165352 A1 * | 7/2005 | Henry | A61F 2/97 604/108 |
| 2006/0025844 A1 * | 2/2006 | Majercak | A61F 2/966 623/1.11 |
| 2006/0142838 A1 * | 6/2006 | Molaei | A61F 2/95 623/1.12 |
| 2006/0200221 A1 * | 9/2006 | Malewicz | A61F 2/966 623/1.11 |
| 2006/0287644 A1 | 12/2006 | Inganas | |
| 2007/0083226 A1 * | 4/2007 | Buiser | A61B 17/12109 606/200 |
| 2007/0112409 A1 | 5/2007 | Wu | |
| 2008/0027528 A1 * | 1/2008 | Jagger | A61F 2/95 623/1.11 |
| 2008/0119943 A1 | 5/2008 | Armstrong | |
| 2008/0132989 A1 * | 6/2008 | Snow | A61F 2/966 623/1.12 |
| 2008/0140178 A1 | 6/2008 | Rasmussen | |
| 2008/0167705 A1 * | 7/2008 | Agnew | A61F 2/97 623/1.12 |
| 2009/0259286 A1 * | 10/2009 | Ohri | A61F 2/97 623/1.11 |
| 2010/0076479 A1 * | 3/2010 | Monstadt | A61B 17/12022 606/191 |
| 2010/0114290 A1 | 5/2010 | Rasmussen | |
| 2010/0262157 A1 | 10/2010 | Silver | |
| 2011/0015718 A1 * | 1/2011 | Schreck | A61F 2/954 623/1.12 |
| 2011/0034987 A1 * | 2/2011 | Kennedy | A61F 2/95 623/1.11 |
| 2011/0137395 A1 * | 6/2011 | Fargahi | A61F 2/95 623/1.11 |
| 2011/0190862 A1 * | 8/2011 | Bashiri | A61F 2/95 623/1.11 |
| 2011/0276121 A1 | 11/2011 | Levine | |
| 2012/0130474 A1 * | 5/2012 | Buckley | A61F 2/97 623/1.12 |
| 2012/0130475 A1 * | 5/2012 | Shaw | A61F 2/82 623/1.12 |
| 2012/0172887 A1 * | 7/2012 | Hatfield | A61F 2/97 606/108 |
| 2014/0142681 A1 * | 5/2014 | Norris | A61F 2/966 623/1.12 |
| 2017/0164951 A1 * | 6/2017 | Divino | A61B 17/12154 |

FOREIGN PATENT DOCUMENTS

| | | |
|---|---|---|
| CN | 102481197 A | 5/2012 |
| DE | 102009056448 A1 | 6/2011 |
| EP | 696447 A2 | 2/1996 |
| EP | 2628470 A2 | 8/2013 |
| FR | 2974727 A1 | 11/2012 |
| JP | 6511408 A | 12/1994 |
| JP | 8173548 A | 7/1996 |
| JP | 8322943 A | 12/1996 |
| JP | 2004528066 A | 9/2004 |
| JP | 2005512634 A | 5/2005 |
| JP | 2008541786 A | 11/2008 |
| JP | 2013500792 A | 1/2013 |
| WO | WO 2005092241 A1 | 10/2005 |

* cited by examiner

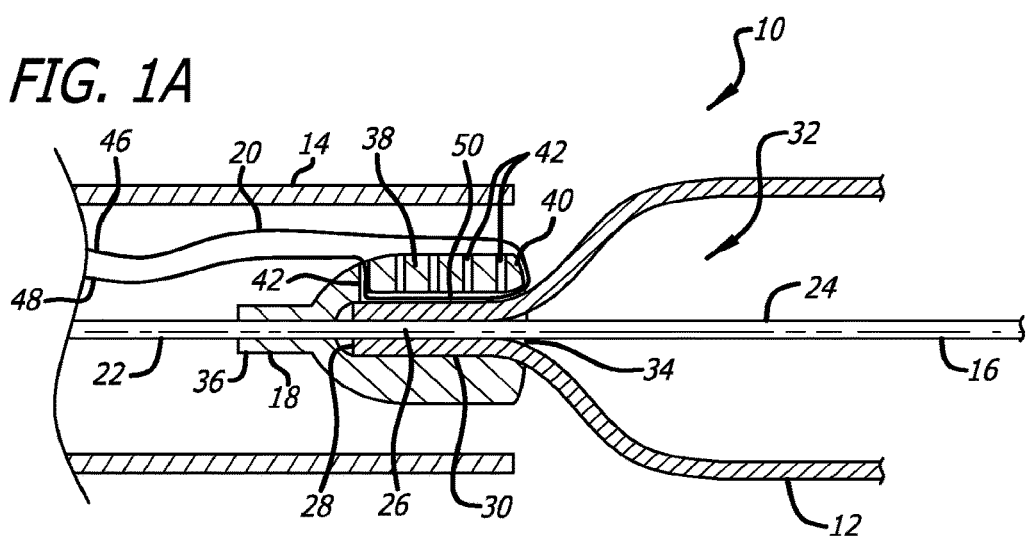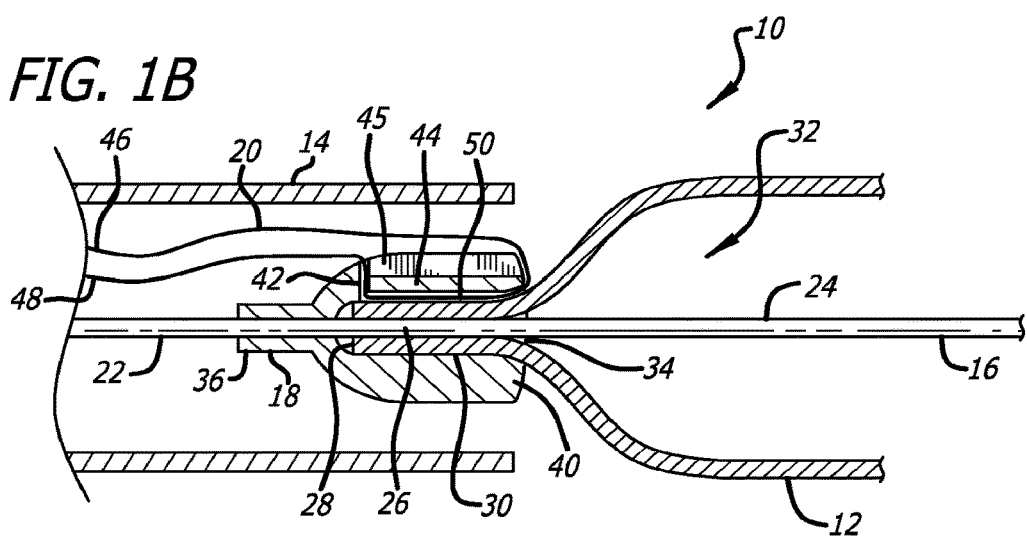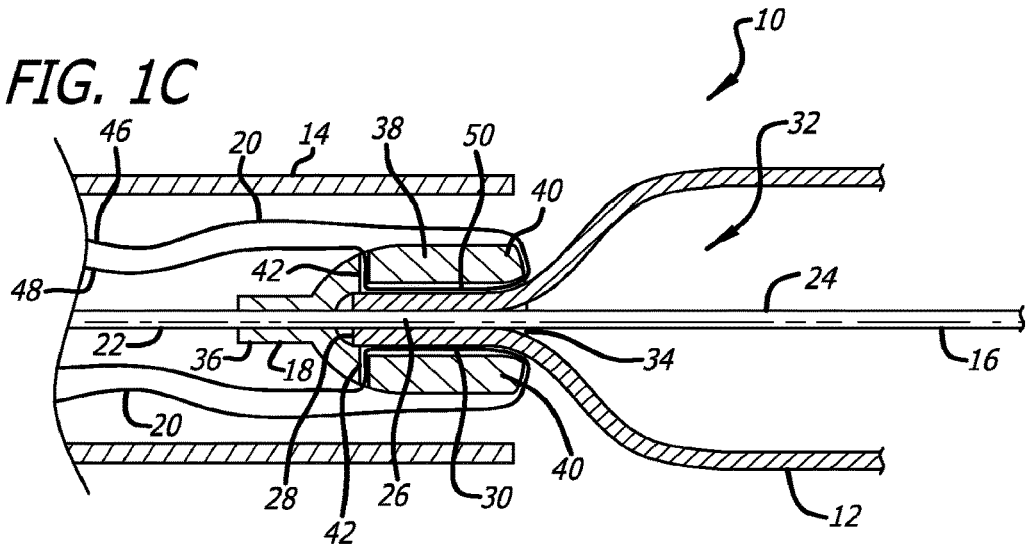

CAPTURE TUBE MECHANISM FOR DELIVERING AND RELEASING A STENT

CROSS REFERENCE TO RELATED PCT APPLICATION

This application is a divisional of U.S. patent application Ser. No. 13/801,728, filed Mar. 13, 2013.

BACKGROUND OF THE INVENTION

This invention relates generally to devices for interventional therapeutic treatment or vascular surgery for treatment of defects in the vasculature, and more particularly concerns a system and method for delivering a self-expanding stent through a catheter to a treatment site in a vasculature of a patient, such as for treatment of aneurysms.

A basic approach to delivery of a self-expanding stent in a patient's vasculature typically involves advancing the stent through a sleeve or microcatheter by pushing the stent distally through the sleeve or microcatheter until the stent emerges from a distal end of the sleeve or microcatheter at a desired location in the patient's vasculature. At that point, the self-expanding stent is unrestrained, and ideally the self-expanding stent deploys at the desired location in the patient's vasculature. However, this basic approach is typically a "push only" system, due to the self-expanding nature of the stent, since once the stent is deployed, the position of the stent can no longer be manipulated forwards or backwards, so that retraction of the stent is typically not possible once the self-expanding stent has been deployed.

In one type of delivery system, a self-expanding stent is radially compressed between two pushing surfaces, one proximal and one distal to the stent, so that as long as the entire self-expanding stent remains inside a sleeve or microcatheter, the self-expanding stent can be advanced and retracted. However, if any portion of the distal end of the stent is revealed outside of the microcatheter, the ability to retract the self-expanding stent is lost, and at that point the delivery system acts essentially the same as a "push only" system. Another type of delivery system is known that utilizes a physical feature on a self-expanding stent to capture a proximal portion. Such a proximal capture type of delivery system allows advancement and retraction, even after a distal portion of the stent has exited a sleeve or microcatheter. However, this type of delivery system requires a certain feature to be included in the stent design, which is not always feasible.

It would be desirable for a system for delivering a self-expanding stent to allow control of both advancement and retraction of the stent, which requires that the delivery system have some type of capture interface with the stent, such as by providing an arrangement on the delivery system allowing capture of all or a portion of the stent, or capture of a particular interfacing feature on the stent. It would be desirable to provide such a capture interface at a proximal end of the stent, so that a distal portion of the stent can be revealed and allowed to deploy to a partial or fully expanded diameter prior to releasing the entire stent from the delivery system, to allow retraction and repositioning of the self-expanding stent before the entire stent is released from the delivery system. It would be desirable to provide such a capture interface as a "positive capture" delivery system for delivering a self-expanding stent, in which the self-expanding stent is held proximally by the delivery system regardless of whether the self-expanding stent is positioned within or wholly outside of a delivery sleeve or microcatheter, so that the entire stent can be advanced out of the distal end of the microcatheter without releasing the stent, and can be subsequently retracted fully back into the delivery sleeve or microcatheter. With such a "positive capture" delivery system it also would be desirable that a separate, deployment action be required in order to release the self-expanding stent, in order to provide the delivery system with a maximal versatility. The present invention meets these and other needs.

SUMMARY OF THE INVENTION

Briefly and in general terms, the present invention provides for a capture tube mechanism for delivering and releasing a self-expanding stent, in which a proximal portion of the stent is removably retained on a core wire by a distal portion of a tubular capture sleeve. The capture tube mechanism permits advancement and retraction of the stent prior to final release, and allows a major portion of the stent except for a small portion of the stent captured by the capture tube mechanism to be expanded outside of a delivery sleeve or microcatheter, while still allowing retraction and repositioning of the stent, without requiring any specific capture feature to be included in the stent design.

Accordingly, in a first embodiment, the present invention provides for an apparatus for delivering and releasing a self-expanding stent through a catheter to a treatment site in a patient's vasculature, the apparatus includes a tubular capture sleeve disposed over a proximal portion of the self-expanding stent, and a core wire having a distal portion extending through at least a portion of an inner lumen of the self-expanding stent, with a proximal portion of the self-expanding stent disposed over an intermediate portion of the core wire. In a presently preferred aspect, a distal portion of the tubular capture sleeve is configured to removably retain the proximal portion of the self-expanding stent within a lumen of the tubular capture sleeve and on the intermediate portion of the core wire. In another presently preferred aspect, the tubular capture sleeve includes one or more apertures extending through the distal portion of the tubular capture sleeve, preferably at a location aligned with the proximal end of the self-expanding stent. One or more elongated members extend through the one or more apertures of the tubular capture sleeve and through the lumen of the tubular capture sleeve and out the distal end of the tubular capture sleeve, with first and second ends of the one or more elongated members extending proximally from the tubular capture sleeve, such that the one or more elongated members are configured to split the tubular capture sleeve when the first and second ends of the one or more elongated members are pulled proximally, to release the proximal end of the self-expanding stent from the tubular capture sleeve and the intermediate portion of the core wire.

In another presently preferred aspect, the intermediate portion of the core wire may optionally have an exterior surface that includes a retaining feature, such as one or more pegs, a plurality of teeth, or a textured high friction surface, for example. In another presently preferred aspect, the distal portion of the tubular capture sleeve is configured to clamp, be compressed over, or otherwise capture the proximal portion of the self-expanding stent within the lumen of the tubular capture sleeve and on the intermediate portion of the core wire. In another presently preferred aspect, the tubular capture sleeve comprises a shrinkable sleeve, or an elastic sleeve, for example.

In another presently preferred aspect, the one or more elongated members may be formed by one or more polymer fibers or wires arranged radially around the tubular capture sleeve, for example. In another presently preferred aspect, the tubular capture sleeve includes one or more perforations along a path between the one or more apertures and the distal end of the tubular capture sleeve, or one or more skives along a path between the one or more apertures and the distal end of the tubular capture sleeve.

In a second embodiment, the present invention provides for an apparatus for delivering and releasing a self-expanding stent through a catheter to a treatment site in a patient's vasculature, including a core wire having a stop member, such as a bump or an enlarged portion of the core wire, positioned between a proximal portion and an intermediate portion of the core wire, with a distal portion of the core wire extending through at least a portion of an inner lumen of a self-expanding stent, and a proximal portion of the self-expanding stent disposed over the intermediate portion of the core wire distally of the stop member of the core wire. A distal portion of a tubular capture sleeve is disposed over the stop member of the core wire and a proximal portion of the self-expanding stent, and the distal portion of the tubular capture sleeve is configured to removably retain the proximal portion of the self-expanding stent within a lumen of the tubular capture sleeve and on the intermediate portion of the core wire. In a presently preferred aspect, the tubular capture sleeve is configured to release the proximal end of the self-expanding stent from the tubular capture sleeve and the intermediate portion of the core wire when the distal portion of the tubular capture sleeve is pulled proximally of the stop member of the core wire.

In another presently preferred aspect, the intermediate portion of the core wire optionally may have an exterior surface includes a retaining feature, such as a high friction surface, for example. In another presently preferred aspect, the tubular capture sleeve comprises a shrinkable sleeve or an elastic sleeve, for example. In another presently preferred aspect, the distal portion of the tubular capture sleeve is configured to clamp, be compressed over, or otherwise capture the proximal portion of the self-expanding stent within the lumen of the tubular capture sleeve and on the intermediate portion of the core wire. In another presently preferred aspect, the proximal portion of the tubular capture sleeve is mechanically linked to the proximal portion of the core wire, such as by an elongated connector member, and wherein the tubular capture sleeve is configured to be pulled proximally via the elongated connector member while the core wire is pushed distally.

In another variation, a second stop member optionally can be provided on the intermediate portion of the core wire, wherein the tubular capture sleeve is configured to removably retain the proximal portion of the self-expanding stent over the second stop member within the lumen of the tubular capture sleeve, and the tubular capture sleeve is configured to release the proximal end of the self-expanding stent from the tubular capture sleeve and the second stop member when the distal portion of the tubular capture sleeve is pulled proximally of the first and second stop members of the core wire while the core wire is pushed distally. In another presently preferred aspect, the second stop member may be formed as a bump or an enlarged portion of the core wire. In another presently preferred aspect, the distal portion of the tubular capture sleeve is configured to clamp, be compressed over, or otherwise capture the proximal portion of the self-expanding stent within the lumen of the tubular capture sleeve and over the second stop member of the core wire.

These and other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 1A is a schematic sectional diagram of a first embodiment of a capture tube mechanism for delivering and releasing a self-expanding stent, showing a self-expanding stent captured by a tubular capture sleeve, according to the present invention.

FIG. 1B is a schematic sectional diagram of a variation of the embodiment shown in FIG. 1A.

FIG. 1C is a schematic sectional diagram of another variation of the embodiment shown in FIG. 1A.

DETAILED DESCRIPTION OF THE PREFERRED EMBODIMENTS

Figure 2A:
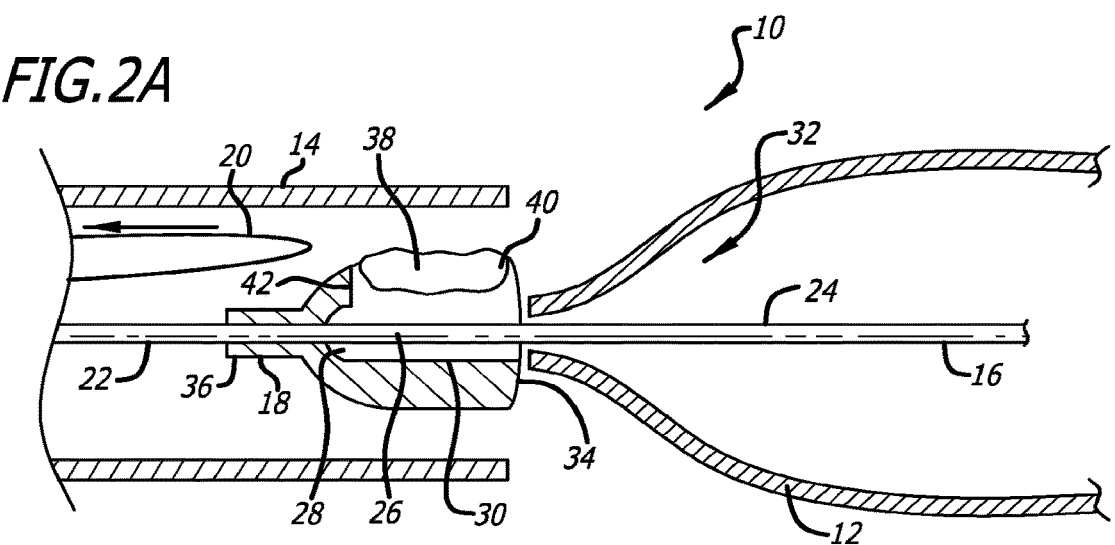
FIG. 2A is a schematic sectional diagram similar to FIG. 1A, showing the self-expanding stent released by the tubular capture sleeve.
Figure 2B:
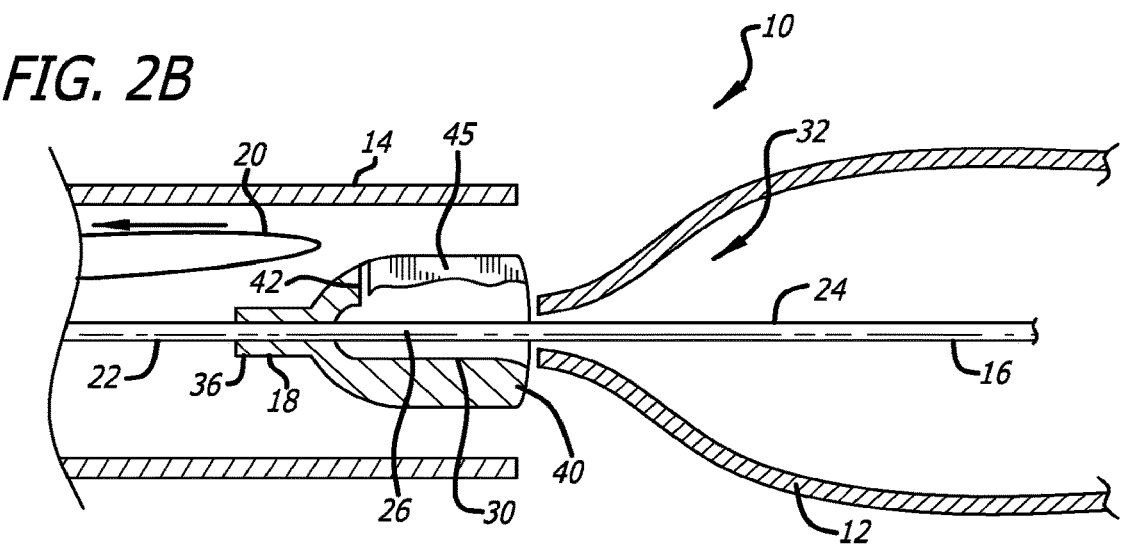
FIG. 2B is a schematic sectional diagram similar to FIG. 1B, showing the self-expanding stent released by the tubular capture sleeve.
Figure 2C:
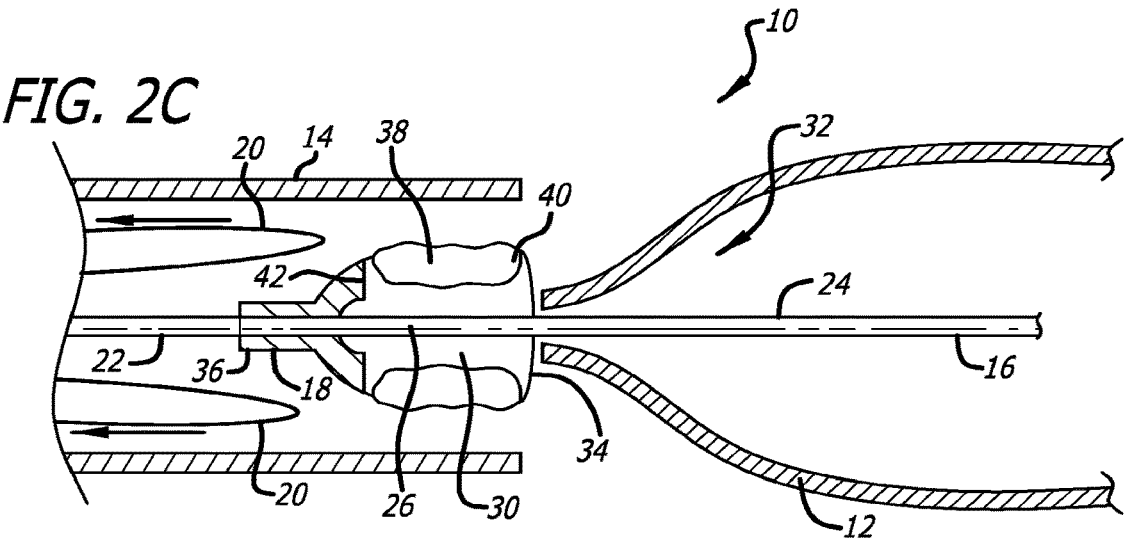
FIG. 2C is a schematic sectional diagram similar to FIG. 1C, showing the self-expanding stent released by the tubular capture sleeve.

Referring to the drawings, which are provided by way of example, and not by way of limitation, in a first embodiment, the present invention provides for an apparatus or delivery system 10 for delivering and releasing a self-expanding stent 12 through a catheter, sleeve or microcatheter 14 to a treatment site in a vasculature of a patient (not shown). As is illustrated in FIGS. 1A to 2C, the delivery system includes a core wire 16, a tubular capture sleeve 18, and one or more elongated members 20 configured to split the tubular capture sleeve to release the self-expanding stent, as will be further explained below. The core wire has a proximal portion 22, a distal portion 24, and an intermediate portion 26 located between the proximal and distal portions of the core wire. In one presently preferred aspect, the intermediate portion of the core wire optionally may have an exterior surface including a retaining feature such as one or more pegs, teeth, or a high friction surface, such as textured metal or a low durometer polymer surface, for example.

The self-expanding stent has a proximal end 28, a proximal portion 30, and an inner lumen 32, and the distal portion of the core wire extends through at least a portion of the inner lumen of the self-expanding stent, with the proximal portion of the self-expanding stent disposed over the intermediate portion of the core wire.

The tubular capture sleeve includes a lumen 34, a proximal portion 36, a distal portion 38, and a distal end 40, and the distal portion of the capture sleeve is disposed over the proximal portion of the self-expanding stent, such that the distal portion of the capture sleeve is configured to removably retain the proximal portion of the self-expanding stent within the lumen of the tubular capture sleeve and on the intermediate portion of the core wire, such as by clamping or compressing the distal portion of the capture sleeve over the proximal portion of the self-expanding stent and onto the intermediate portion of the core wire, or by otherwise capturing at least a portion of the proximal portion of the self-expanding stent. The tubular capture sleeve may be a shrinkable or elastic sleeve, for example, and preferably includes one or more apertures 42 that extend radially through the distal portion of the tubular capture sleeve at a location substantially aligned with the proximal end of the self-expanding stent, as is illustrated in FIG. 1A.

Referring to FIG. 1B, in one variation, the tubular capture sleeve may include one or more thinned diameter portions or skives 44 along a path between the one or more apertures and the distal end of the tubular capture sleeve, leaving an interior wall 45 extending partially radially through the distal portion of the tubular capture sleeve.

The one or more elongated members have a first end 46, a second end 48, and an intermediate portion or loop 50 between the first and second ends of the elongated member, and the intermediate portion of the one or more elongated members preferably extend through a most proximal one of the corresponding one or more apertures of the tubular capture sleeve, through the lumen of the tubular capture sleeve and out the distal end of the tubular capture sleeve. The first and second ends of the one or more elongated members extend proximally from the tubular capture sleeve, and the one or more elongated members are configured to split the tubular capture sleeve, shown at 51, when the first and second ends of the one or more elongated members are pulled proximally to release the proximal end of the self-expanding stent from the tubular capture sleeve and the intermediate portion of the core wire. In a presently preferred aspect, the one or more elongated members may be one or more rip-cord style polymeric fibers or metal wires, for example, and in another variation, may be provided as a plurality of rip-cord style polymeric fibers or metal wires arranged radially around the tubular capture sleeve, as is illustrated in FIG. 1C.

Figure 3A:
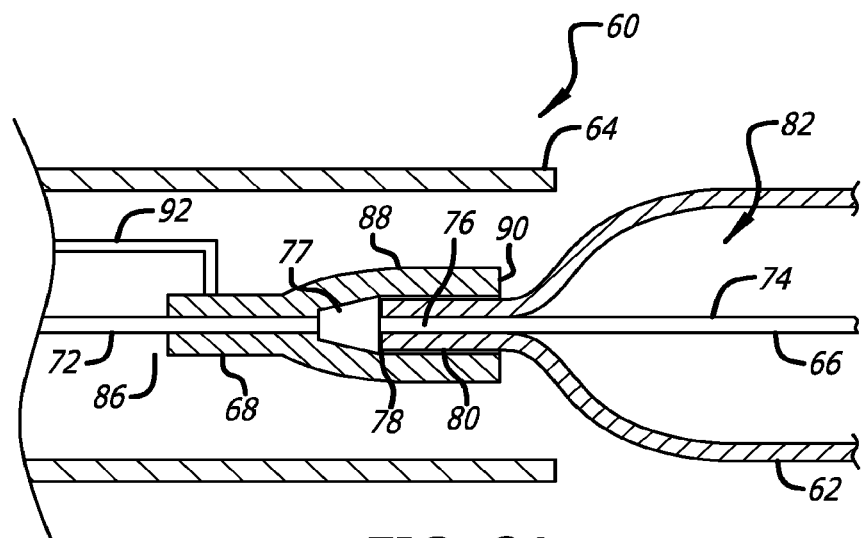
FIG. 3A is a schematic sectional diagram of a second embodiment of a capture tube mechanism for delivering and releasing a self-expanding stent, showing a self-expanding stent captured by a tubular capture sleeve, according to the present invention.
Figure 3B:
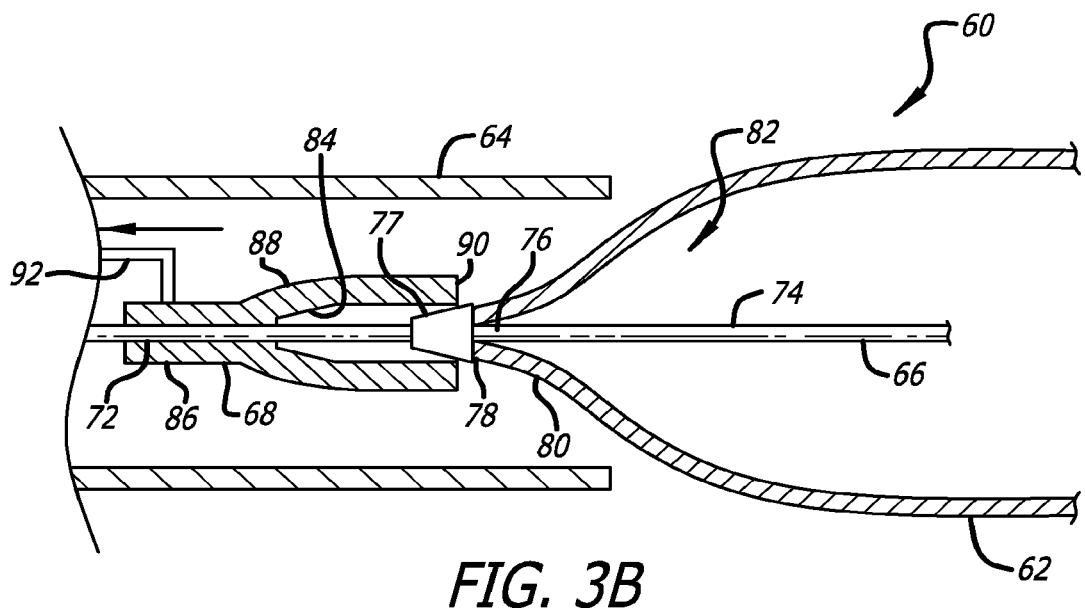
FIG. 3B is a schematic sectional diagram similar to FIG. 3A, showing the self-expanding stent released by the tubular capture sleeve.

Referring to FIGS. 3A and 3B, in a second embodiment, the present invention provides for an apparatus or delivery system 60 for delivering and releasing a self-expanding stent 62 through a catheter, sleeve or microcatheter 64 to a treatment site in a vasculature of a patient (not shown). The delivery system includes a core wire 66 and a tubular capture sleeve 68, which can be pulled proximally while the core wire is pushed distally, to release the self-expanding stent, as will be further explained below. The core wire has a proximal portion 72, a distal portion 74, an intermediate portion 76 located between the proximal and distal portions of the core wire, and a stop member 77 positioned between the proximal portion and the intermediate portion. The stop member can be formed as a bump or enlarged portion of the core wire having a larger diameter or thickness than the adjacent proximal and intermediate portions, formed either uniformly and symmetrically on the core wire, or non-uniformly and asymmetrically on the core wire. In one presently preferred aspect, the intermediate portion of the core wire optionally may have an exterior surface including a retaining feature such as one or more pegs, teeth, or a high friction surface, such as textured metal or a low durometer polymer surface, for example.

The self-expanding stent has a proximal end 78, a proximal portion 80, and an inner lumen 82, through at least a portion of which the distal portion of the core wire extends, with the proximal portion of the self-expanding stent disposed over the intermediate portion of the core wire distally of the stop member of the core wire.

The tubular capture sleeve includes a lumen 84, a proximal portion 86, a distal portion 88 and a distal end 90, and the distal portion of the capture sleeve is disposed over the stop member of the core wire and the proximal portion of the self-expanding stent. In a presently preferred aspect, the distal portion of the capture sleeve is configured to removably retain the proximal portion of the self-expanding stent within the lumen of the tubular capture sleeve and on the intermediate portion of the core wire, such as by clamping or compressing the distal portion of the capture sleeve over the proximal portion of the self-expanding stent onto the intermediate portion of the core wire, or by otherwise capturing at least a portion of the proximal portion of the self-expanding stent, and the tubular capture sleeve is configured to release the proximal end of the self-expanding stent from the tubular capture sleeve and the intermediate portion of the core wire when the distal portion of the tubular capture sleeve is pulled proximally of the stop member of the core wire. The tubular capture sleeve may be a shrinkable or elastic sleeve, for example. In another presently preferred aspect, the proximal portion of the tubular capture sleeve is mechanically linked, such as by an elongated connector member 92 or a further extension of the proximal portion of the tubular capture sleeve, for example, to be moved relative to the proximal portion of the core wire, so that the tubular capture sleeve can be pulled proximally while said core wire is pushed distally, to release the self-expanding stent.

Figure 3C:
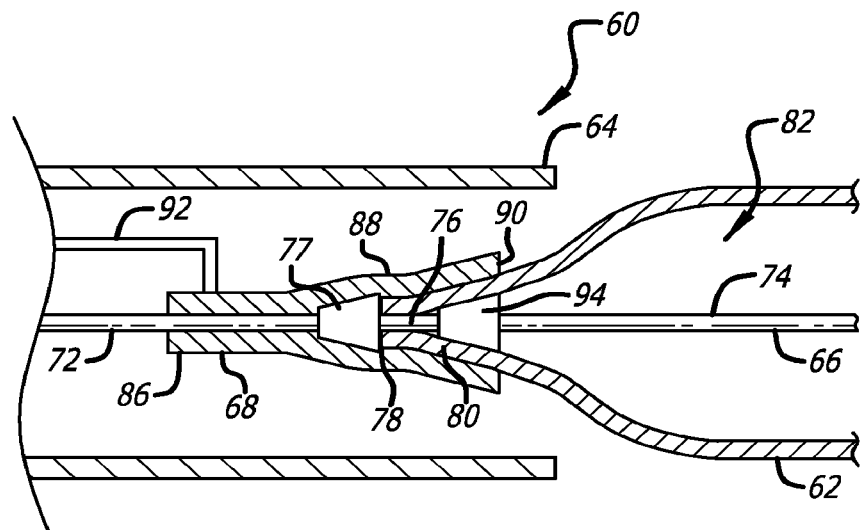
FIG. 3C is a schematic sectional diagram similar to FIG. 3A, showing a variation including a second stop member on an intermediate portion of the core wire.
Figure 3D:
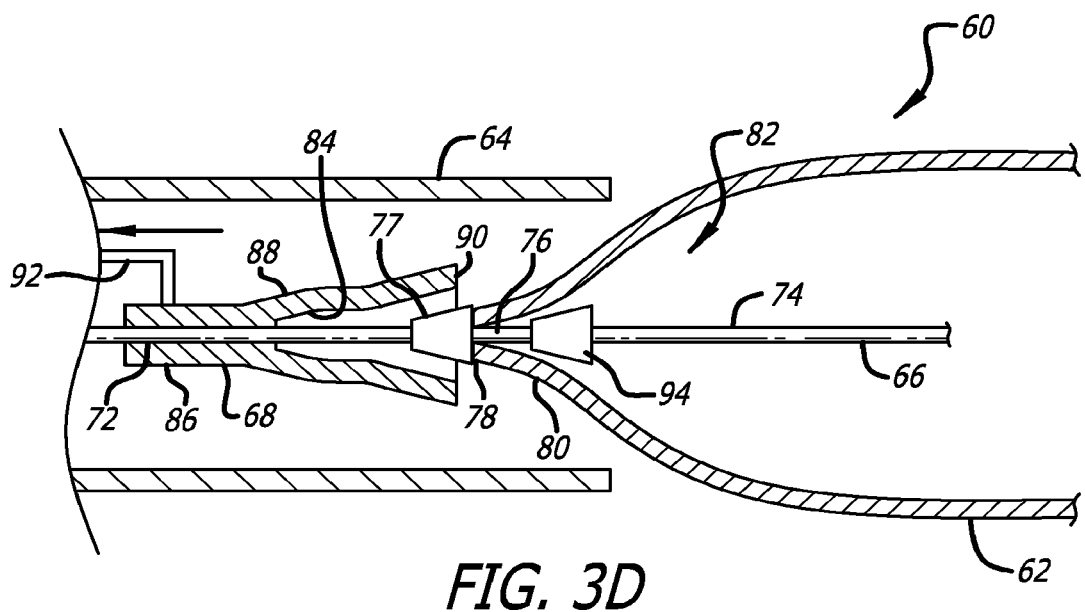
FIG. 3D is a schematic sectional diagram similar to FIG. 3C, showing the self-expanding stent released by the tubular capture sleeve.

Referring to FIGS. 3C and 3D, in another variation, a second stop member 94 optionally can be provided on the intermediate portion of the core wire. The tubular capture sleeve preferably is configured to removably retain the proximal portion of the self-expanding stent over the second stop member within the lumen of the tubular capture sleeve, and to release the proximal end of the self-expanding stent from the tubular capture sleeve and the second stop member when the distal portion of the tubular capture sleeve is pulled proximally of the first and second stop members of the core wire while the core wire is pushed distally. This second stop member acts like a stopper or cork to additionally retain the self-expanding stent in the capture sleeve. When detachment is desired, moving the core wire distally relative to the capture sleeve also releases the self-expanding stent from the second stop member, and the first stop member 77 pushes the self-expanding stent out of the capture sleeve. In another presently preferred aspect, the second stop member may be formed as a bump or an enlarged portion of the core wire. In another presently preferred aspect, the distal portion of the tubular capture sleeve is configured to clamp, be compressed over, or otherwise capture the proximal portion of the self-expanding stent within the lumen of the tubular capture sleeve and over the second stop member of the core wire.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. Apparatus for delivering and releasing a self-expanding stent through a catheter to a treatment site in a patient's vasculature, comprising:
   a core wire having a proximal portion, a distal portion, and an intermediate portion located between said proximal and distal portions of said core wire;
   a self-expanding stent having a proximal end, a proximal portion and an inner lumen, said distal portion of said core wire extending through at least a portion of said inner lumen of said self-expanding stent, with said proximal portion of said self-expanding stent disposed over said intermediate portion of said core wire;
   a tubular capture sleeve having a lumen, a proximal portion, a distal portion and a distal end, said distal portion of said tubular capture sleeve disposed over said proximal portion of said self-expanding stent, and said distal portion of said tubular capture sleeve being configured to removably retain said proximal portion of said self-expanding stent within said lumen of said tubular capture sleeve and on said intermediate portion of said core wire, said tubular capture sleeve including at least one aperture extending through said distal portion of said tubular capture sleeve at a location aligned with the proximal end of said self-expanding stent; and
   at least one elongated member having first and second ends and an intermediate portion between said first and second ends of said elongated member, said intermediate portion of said at least one elongated member extending through said at least one aperture of said tubular capture sleeve and through said lumen of said tubular capture sleeve and out said distal end of said tubular capture sleeve, said first and second ends of said at least one elongated member extending proximally from said tubular capture sleeve, and said at least one elongated member being configured to split said tubular capture sleeve when said first and second ends of said at least one elongated member are pulled proximally to release said proximal end of said self-expanding stent from said tubular capture sleeve and said intermediate portion of said core wire.

2. The apparatus of claim 1, wherein said distal portion of said tubular capture sleeve is configured to clamp said proximal portion of said self-expanding stent within said lumen of said tubular capture sleeve and on said intermediate portion of said core wire.

3. The apparatus of claim 1, wherein said distal portion of said tubular capture sleeve is configured to be compressed over said proximal portion of said self-expanding stent within said lumen of said tubular capture sleeve and on said intermediate portion of said core wire.

4. The apparatus of claim 1, wherein said distal portion of said tubular capture sleeve is configured to capture said proximal portion of said self-expanding stent within said lumen of said tubular capture sleeve and on said intermediate portion of said core wire.

5. The apparatus of claim 1, wherein said tubular capture sleeve comprises a shrinkable sleeve.

6. The apparatus of claim 1, wherein said tubular capture sleeve comprises an elastic sleeve.

7. The apparatus of claim 1, wherein said at least one elongated member comprises a plurality of polymer fibers arranged radially around the tubular capture sleeve.

8. The apparatus of claim 1, wherein said at least one elongated member comprises a plurality of wires arranged radially around the tubular capture sleeve.

9. The apparatus of claim 1, wherein said tubular capture sleeve includes at least one perforation along a path between said at least one aperture and said distal end of said tubular capture sleeve.

10. The apparatus of claim 1, wherein said tubular capture sleeve includes at least skive along a path between said at least one aperture and said distal end of said tubular capture sleeve.

11. The apparatus of claim 1, wherein said proximal portion of said tubular capture sleeve is mechanically linked to the proximal portion of the core wire, and wherein said tubular capture sleeve is configured to be pulled proximally while said core wire is pushed distally.

12. The apparatus of claim 11, wherein said proximal portion of said tubular capture sleeve is mechanically linked to the proximal portion of the core wire by an elongated connector member.

* * * * *